United States Patent
Koh et al.

(10) Patent No.: US 6,254,620 B1
(45) Date of Patent: Jul. 3, 2001

(54) SURGICAL THREAD CUTTER

(75) Inventors: Charles Koh, Mamequon, WI (US); Horst Dittrich, Immendingen (DE); Simon Solingen, Los Angeles, CA (US)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/155,879

(22) PCT Filed: Feb. 6, 1998

(86) PCT No.: PCT/EP98/00669

§ 371 Date: Mar. 15, 1999

§ 102(e) Date: Mar. 15, 1999

(87) PCT Pub. No.: WO98/34545

PCT Pub. Date: Aug. 13, 1998

(30) Foreign Application Priority Data

Feb. 7, 1997 (DE) .............................................. 197 04 580

(51) Int. Cl.[7] .................................................. A61B 17/32
(52) U.S. Cl. ........................ 606/167; 606/182; 30/278; 30/280
(58) Field of Search .................................. 606/182, 167, 606/170, 181, 83, 148, 174, 185, 190; 600/552, 564; 30/241, 279.2, 278, 280, 338, 211, 214, 366, 368, 184

(56) References Cited

U.S. PATENT DOCUMENTS

| 1,010,817 | * | 12/1911 | Strong | 30/280 |
|---|---|---|---|---|
| 3,328,876 | | 7/1967 | Hoppe . | |
| 3,372,477 | | 3/1968 | Hoppe . | |
| 3,747,690 | * | 7/1973 | Deike | 173/118 |
| 3,802,074 | | 4/1974 | Hoppe . | |
| 5,304,190 | * | 4/1994 | Reckelhoff et al. | 606/170 |
| 5,364,365 | * | 11/1994 | Wortrich | 604/158 |
| 5,549,623 | | 8/1996 | Sharpe et al. . | |
| 5,556,407 | | 9/1996 | Wurster et al. . | |

FOREIGN PATENT DOCUMENTS

| 91 09 097 | 10/1991 | (DE) . |
|---|---|---|
| 91 12 301 | 1/1992 | (DE) . |
| 92 14 580 | 4/1994 | (DE) . |
| 42 04 051 C2 | 12/1994 | (DE) . |
| 197 04 580 C2 | 1/1999 | (DE) . |

OTHER PUBLICATIONS

Brochure for "Storz Endoskope," 1 page featuring different kinds of surgical thread cutters.

* cited by examiner

Primary Examiner—Henry J. Recla
Assistant Examiner—Anthony S. King
(74) Attorney, Agent, or Firm—St. Onge Steward Johnston & Reens LLC

(57) ABSTRACT

A surgical thread cutter (10) has a blade (18) movable via an actuation mechanism (30) relative to an anvil (20) toward and away from the latter, and a spring by way of which the blade (18) can be acted upon by spring force in one movement direction. In the interest of better and safer handling, it is proposed that the spring act upon the blade (18) in the cutting direction, that a retention system be provided by means of which the blade (18) can be locked in a position remote from the anvil (20); and that the force of the spring be set in such a way that after the retention system is released, the blade (18) can be moved onto the anvil (20) in the manner of a guillotine (FIG. 1).

23 Claims, 1 Drawing Sheet

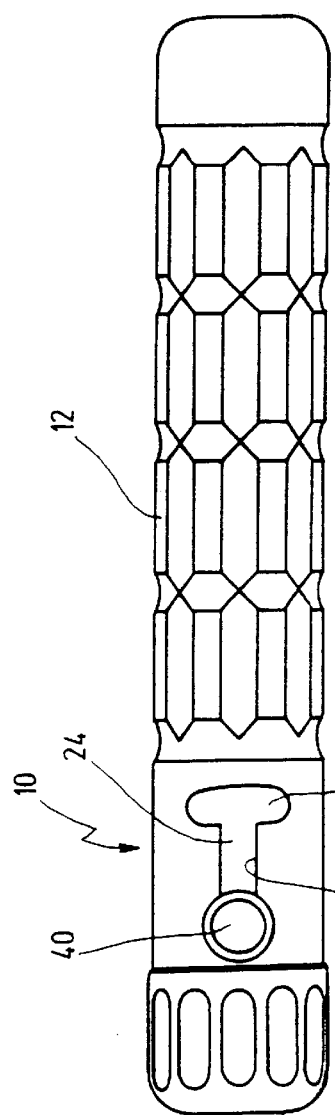
Fig. 1
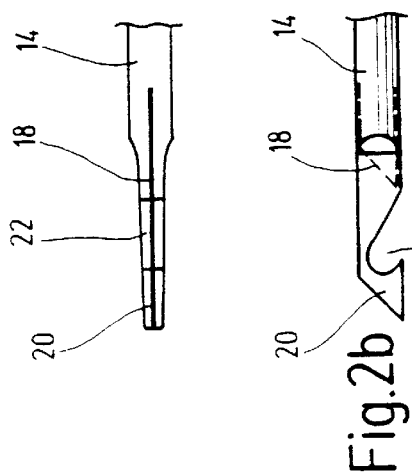
Fig. 2a
Fig. 2b
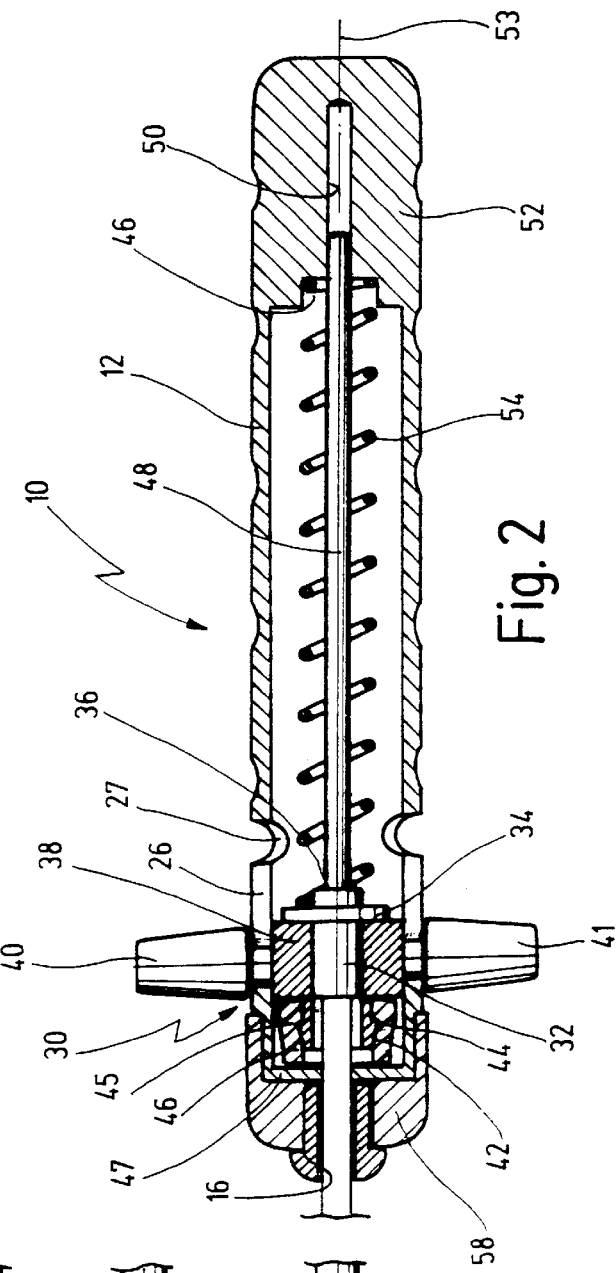
Fig. 2

SURGICAL THREAD CUTTER

FIELD OF THE INVENTION

The present invention relates to a surgical thread cutter having a blade movable via an actuation mechanism relative to an anvil toward and away from the latter, and having a spring by way of which the blade can be acted upon by spring force in one movement direction.

BACKGROUND OF THE INVENTION

Surgical thread cutters of this kind are utilized to cut a thread material that is used for intracorporeal sutures. It has been found that it is difficult to cut the thread material with the dissecting scissors normally used for cutting tissue. It has been found in particular that the threads get caught in the scissors.

DE 92 14 580.9 U1 discloses a surgical thread cutter which has a sharp blade that moves toward a flat anvil and thereby cuts the thread. For this purpose, blade and anvil are movable relative to one another; the movement is controlled via handle elements such as those ordinarily used in medical scissors, which are joined to one another via a hinge. The anvil has a slot into which the sharp blade can travel, thus cutting through the thread which is pressed against the anvil.

The applicant's company brochure entitled "Endoskopische Chirurgie, 2. Ausgabe 1/94, Kapitel 8, Naht und Ligatur, Seite NH 4 A" [Endoscopic surgery, 2nd edition 1/94, Chapter 8, Sutures and ligatures, page NH 4 A] makes known a surgical thread cutter using the aforementioned Scarfi principle, in which the blade is received so as to move back and forth in a shaft at whose distal end the anvil is arranged. A rod-shaped actuation element joined to the blade passes through the shaft, and that element is joined at the proximal end to an annular handle element. Extending parallel to the shaft at the proximal end, i.e. parallel to the shaft axis, is a spring which braces at one end against the annular handle element and at the other end against a further handle element mounted in stationary fashion on the shaft. The spring is preloaded in such a way that the annular handle element, together with the actuation element and the blade mounted thereon, is pushed away from the anvil, so that space exists between the blade edge and the anvil so as to introduce between the blade and anvil the thread that is to be cut through. To cut through the thread, the distal end of the thread cutter is brought against the thread in such a way that the latter ends up between blade and anvil, the thread cutter itself being introduced, for example, through a trocar into the body. To cut through the thread, the annular handle element at the proximal end is displaced in the distal direction relative to the stationary handle element against the force of the spring, thus moving the blade toward the anvil and cutting through the thread received between them.

DE 42 04 051 C2 discloses an anvil scissors for surgical purposes in which the blade is arranged so that as a function of the thread thickness and the material being cut, the greater the resistance presented to closure of the blade by the material being cut, the stronger the pulling cut. In this context the blade is pivotable about an axis, and movable toward and away from the anvil.

DE 91 09 097 U1 discloses a retaining forceps which contains a spring which generates a preload in order to act upon the two forceps arms in the closing direction. This is a thread holding apparatus. A retaining apparatus serves to displace one forceps arm.

DE 91 12 301 U1 discloses a needle holder which has a rod that is surrounded by a sleeve which is movable axially relative to the rod. The sleeve is displaceable, and is preloaded by a spring against a radial contact surface.

Documents U.S. Pat. Nos. 3,802,074, 3,328,876, and 3,372,477 concern thread cutters in which the blade can be moved back and forth along a shaft-like part, specifically by the hand or a finger of the actuating person who is holding the thread cutter in his or her hand. The cutting movement and the cutting action are thus determined by the particular individual hand strength and dexterity of the operator.

It has been found in practical use that the anvil can press the thread against the anvil and push the latter, without cutting through it, into the slot in the anvil rather than cutting through the thread. In this context, the blade can get caught on the thread in such a way that the force of the spring is not sufficient to pull the blade back away from the anvil.

In addition, it has been found in disadvantageous fashion that the skill of the operator substantially determines whether the thread can be cut through with only a single blade movement, or whether several movements are necessary for the purpose. In any event, it has been found that close attention is required when cutting through the thread.

SUMMARY OF THE INVENTION

It is the object of the present invention to provide a remedy here, and to develop a surgical thread cutter of the kind cited initially in such a way that the latter operates reliably, and in particular immediately cuts through the thread with a single cutting attempt.

According to the present invention, the object is achieved in that the spring acts upon the blade in the cutting direction; that a retention system is provided by means of which the blade can be locked in a position remote from the anvil; and that the force of the spring is set in such a way that after the retention system is released, the blade can be moved onto the anvil in the manner of a guillotine.

When the retention system is released, the spring has pushed the blade into the anvil. This represents a defined end position of the blade in which, while the distal end is being brought to the point in the body to be cut, no tissues or the like can enter between the blade and anvil. To prepare for the cutting operation, the blade is moved via the actuation mechanism away from the anvil against the force of the spring, and retained in that position. The thread can now be brought between the blade and anvil. The force of the cocked compression spring is set so that after the retention system is released, the blade is moved very quickly, i.e. in the manner of a guillotine, onto the anvil. This rapid movement with the assistance of the corresponding compressive force of the spring ensures that the thread is cut through immediately by the blade, and is not entrained by it or even pushed into the slot in the anvil. Although it has only a small mass, the thread represents a mass at rest with respect to the very rapidly moving thread, so that when the blade reaches the thread it immediately digs into its material before the latter can even move out of its rest position. This immediately creates an initial cutting point which allows the further cutting operation to proceed in definitive fashion, i.e. cuts through the thread, without allowing the thread ends on either side of the blade to be moved, i.e. entrained by the blade. If a thread of this kind has been used, for example, to suture a wound, rapid detachment of this kind, which exerts no tensile forces on the thread, does not cause any impairment of the sutured operative area. After the cutting operation the blade is extended into the anvil, and the thread cutter can be pulled out of the body with no risk that tissues will become caught in the recessed region between blade and anvil, possibly damaging the tissue. The spring can be arranged proximally or distally depending on the design circumstances.

In a further embodiment of the invention, the actuation mechanism is movable along the movement direction of the blade, and is rotatable relative to the movement direction and can be retained by the retention system in a rotated position.

The feature, known per se, according to which the actuation mechanism is movable along the movement direction of the blade has the advantage that as the blade is moved, no tilting moments are exerted on the thread cutter, as is the case, for example, with the aforecited scissors handle elements with hinge joint. The ability to be rotated and retained means that after the blade has been pulled away from the anvil, the actuation mechanism can be retained by simple rotation, and the retention system can be released again by way of an opposite rotational movement. Such movements are easy to perform with one hand without close attention, so that the operator's attention can remain concentrated at the distal end of the thread cutter in order to hold the thread that is to be cut off or cut through in a suitable position between the anvil and blade.

In a further embodiment of the invention, the actuation mechanism is received proximally in a handle-like housing.

The advantage of this feature is that the thread cutter can be grasped via the housing, and the actuation mechanism can be moved using fingers of the hand which has grasped the housing. This allows for simple one-handed operation.

In a further embodiment of the invention, the retention mechanism has at least one actuation element, projecting radially from the actuation mechanism, which extends through a bayonet guide in the housing.

This feature has the considerable design advantage that the housing not only surrounds the movement mechanism in protective fashion, but at the same time is also configured in simple fashion as a constituent of the retention system. The at least one radially projecting actuation pin can be moved against the force of the spring using one finger of the hand which is holding the handle element, the bayonet guide unequivocally controlling this movement. By way of a slight circumferential rotation of the actuation element into a lateral cutout of the bayonet guide, the actuation mechanism can then be retained in that position. Gentle finger pressure is then sufficient to pivot the actuation pin back again and release the guillotine-like movement of the blade toward the anvil. The operations of cocking, retaining, and releasing the retaining system can be performed without particular attention, and can be performed without visual attention by simply feeling for and moving the actuation element.

In a further embodiment of the invention, two diametrically opposite, radially projecting actuation pins are provided.

The advantage of this feature is that one hand constituents of simple configuration are provided, which can be grasped, for example, with two fingers and can easily be moved in order to control the actuation mechanism. To cock the actuation mechanism, the two pins merely need to be pulled back and then rotated slightly in order to lock the retention mechanism.

In a further embodiment of the invention, the bayonet guide is configured as a T-shaped slot opening in the housing.

The transverse regions of the T now allow the actuation pins, after they have been displaced along the long part of the T to cock the spring, to be slid either to the left or to the right into a transverse region, depending on what is favorable for the operator or what he or she desires. There is thus no need to devote additional attention to whether the actuation pins need to be rotated clockwise or counterclockwise after the actuation mechanism has been cocked.

In a further embodiment of the invention, the transverse regions of the T-shaped slot openings, which extend in the circumferential direction of the housing, are inclined somewhat in the direction of the anvil.

The advantage of this feature is that because of the inclined arrangement in the direction of the anvil, the actuation pins are pressed by the force of the spring against the inclined distal flank of the groove, and moved slightly toward the anvil. When the retention system is released, the pins need to be not only rotated, but simultaneously pulled back somewhat a way from the anvil, which is brought about by the distal flank of the slot. As a result, a displacement or rotation of the actuation pins out of the retaining position must be performed with the application of somewhat more force than in the case of an exactly perpendicular T-shaped slot opening. This prevents the retention system from being released merely by inadvertent contact with the pins.

In a further embodiment of the invention, the spring is arranged in the handle-like housing.

The advantage of this feature is that, particularly together with the feature that the further actuation mechanism is also arranged in the handle, these components are received in protected fashion in the housing, which also contributes to operating reliability.

In a further embodiment of the invention, a damping member is provided which damps the movement of the blade at the end of the cutting movement.

Provision is particularly made, in this context, for the actuation mechanism to have a damping member which damps the impact of the actuation mechanism against a stop at the end of the cutting movement.

The advantage of this feature is that at the end of the movement operation, i.e. after the thread has been cut through, the impact of the actuation element against a stop is damped, so that there is no risk that the thread cutter will be moved unfavorably into the patient by the impact pressure or recoil.

In a further embodiment of the invention, there is provided in the housing an elastic damping member which strikes against an inner wall of the housing and in that context is deformable.

The advantage of this feature is that the damping member is also received in the housing, so that not only is the mechanical impact damped, but the impact noise is also damped. The elastic element is also protected by the housing from mechanical damage.

In a further embodiment of the invention, the blade is received in a shaft, and the shaft and blade are detachable from one another.

The advantage of this feature is on the one hand that the blade is received and reliably guided in the shaft, and that the blade and shaft can be detached from one another for cleaning purposes.

In a further embodiment of the invention, the anvil is in the shape of a hook.

The advantage of this feature is that because the anvil is configured as a hook, the thread to be cut through can be gripped by the anvil and can be brought or pulled into the correct position. It is thus also possible, for example if a thread end is to be cut off, to bring it with the hook into a favorable position, i.e. one easily visible to the operator, for example into the field of view of an endoscope, so that the cutting operation can then be performed in controlled fashion.

In a further embodiment of the invention, a tip of the hook faces toward a tip of the blade.

The advantage of this feature is that the tips to be moved relative to one another immediately close off the internal hook space, i.e. after the tip of the blade has reached the level of the tip of the anvil, so that the thread is then caught in lossproof fashion and can no longer inadvertently escape from the hook space in front of the anvil. This results in particularly reliable cutting of the thread.

In a further embodiment of the invention, the anvil is part of the shaft, and the shaft can be detachably joined to the handle-like housing.

The advantage of this feature is that few components are necessary, and they can be easily disassembled for cleaning.

In a further embodiment of the invention, the anvil has a longitudinal slot into which the blade can be extended.

The advantage of this feature is that the blade can be extended into the anvil in reliably guided fashion, and remains there in the relaxed end position. This also ensures that exposed tip of the blade is received in protected fashion in the anvil, so that injuries to handling persons after performing the cut are ruled out.

In a further embodiment of the invention, the blade runs along a surface of the anvil.

The advantage of this feature is that the blade can carry along the thread that is to be cut, and can cut it when striking the surface of the anvil.

In a further embodiment of the invention, the blade has a cutting edge which coacts with an edge of the anvil.

The advantage of this feature is that the blade and the edge of the anvil interact with one another like two scissor elements, thus bringing about a scissor-like cut which is advantageous with many thread materials.

In a further embodiment of the invention, the length of the travel of the blade is adjustable.

The considerable advantage of this feature is that the acceleration travel of the blade can be variably adjusted depending on the thread thickness, thread type, or also in order to compensate for spring fatigue.

In a further embodiment of the invention, the spring is configured as a helical spring, as a compressed-air spring, or as a magnetically cocked spring.

These spring embodiments allow slender designs which can be housed in the handle element and, in particularly advantageous fashion, allow the blade to be driven forward in guillotine-like fashion.

In a further embodiment of the invention, the surgical thread cutter is part of a multifunctional instrument.

In this embodiment, the operations of suturing and cutting off the suture thread can be performed with a single multifunctional instrument, with no need to bring different instruments in succession to the operative point, or to withdraw a suturing instrument first before a thread cutter can be used.

It is understood that the features mentioned above and those yet to be explained below can be used not only in the respective combinations indicated, but also in other combinations or in isolation, without leaving the context of the present invention.

BRIEF DESCRIPTION OF THE DRAWINGS

The invention will be described in more detail and explained below with reference to a selected exemplifying embodiment. In the drawings:

FIG. 1 shows a side view of a thread cutter according to the present invention in which the blade is extended into the anvil;

FIG. 2 shows a longitudinal section of the thread cutter of FIG. 1, in a position rotated 90 degrees about its longitudinal axis;

FIG. 2a shows a side view only of the distal end, in an intermediate state in which the blade is moved away from the anvil; and FIG. 2b shows a depiction corresponding to FIG. 2a, with the blade in the completely pulled-back state.

DETAILED DESCRIPTION

A thread cutter according to the present invention, designated in its entirety in the Figures with the reference character 10, has an elongated rod-shaped housing 12 from which a relatively long cylindrical shaft 14 projects. An actuation element 16 received in the interior of the hollow shaft 14 is joined at the distal end to a sharp blade 18.

Provided at the distal end of shaft 14 is an anvil 20 which is divided in the middle by a longitudinal slot 22 into which the narrow blade 18 can be inserted to fit.

A bayonet guide 24 in the form of a T-slot opening 26 is provided in the wall of housing 12.

The elongated region of the "T" extends along the longitudinal axis of shaft 14 and the longitudinal axis of housing 12, and the transverse region 27 is located proximally and extends in the circumferential direction of housing 12.

Bayonet guide 24 is a constituent of a retaining system 28 for an actuation mechanism 30 received in the housing.

Actuation mechanism 30 (see in particular the sectioned depiction of FIG. 2) has a central cylindrical part 32 which is arranged along the longitudinal center axis of housing 12. Cylindrical part 32 is joined distally to actuation element 16.

Projecting proximally from cylindrical part 32 is a radial annular flange 34; a stem 36 projects axially from annular flange 34.

A sleeve 38 is slid over the cylindrical part and comes to rest against annular flange 34.

The open inside diameter of sleeve 38 is such that it rests against the exterior of cylindrical part 32, but is rotatable about the latter.

Projecting radially and diametrically opposite one another from sleeve 38 are two actuation pins 40 and 41 which pass through T-slot openings 26 of bayonet guide 24 that are correspondingly located diametrically opposite one another.

A tubular flange 42 having a peripheral shoulder 44 projects distally from sleeve 38.

A hollow cylindrical damping member 45 in the form of an elastic element 46, which is produced from an elastic material, is slid over tubular flange 42.

Shoulder 44 is configured so that elastic element 46 can be slid onto tubular flange 42, but is inhibited from being pulled off. Proximally, the annular end of damping member 46 rests against a shoulder between sleeve 38 and the smaller-diameter tubular flange 42.

The axial length of damping member 45 is longer than the length of tubular flange 42, so that distally, the tubular elastic element 46 projects beyond tubular flange 42.

Stem 36 projecting proximally from annular flange 34 is joined to a rod 48 which extends through the hollow interior of housing 12 into a blind hole 50 in proximal end piece 52 of housing 12. In the position shown in FIG. 2, rod 48 extends only slightly into blind hole 50, which serves simultaneously as a guide cylinder for rod 48. Blind hole 50 opens toward the interior of housing 12 into a somewhat wider depression 46. Arranged in the interior around rod 48 is a helical spring 54 whose one end is braced in depression 46 in end piece 52, and whose other end is braced against annular flange 34. Spring 54 is preloaded slightly in tension, and thus pushes actuation mechanism 30 into the position shown in FIGS. 1 and 2. In this position, the distal end of damping member 45 is pressed against an end-surface terminating wall 47 of housing 12.

A nut 58 serves to join shaft 14 to housing 12.

It is apparent from FIG. 2 that anvil 20 is configured as a hook 60; a tip 62 of hook 60 faces a tip 64 of blade 18.

A cutout 68 is cut away in the region of anvil 20 so that the thread to be cut can be laid therein. Hook 60 facilitates capture and placement of the thread.

In order to cut through a thread, thread cutter 10 is grasped via housing 12, and two fingers are used to move actuation pins 40 and 41 against the force of spring 54 from distal to proximal, guiding them in bayonet guide 24. Once actuation pins 40 and 41 have been pulled back to the level of transverse region 27 of T-slot opening 26, they are slightly rotated circumferentially and enter one of transverse regions 27. This was achieved by the fact that sleeve 38 is freely rotatable relative to cylindrical piece 32 which is only axially displaceable. Rotation of the latter is prevented by a corresponding mechanical lock or the like. In this position, actuation mechanism 30 is cocked and retained. Blade 18 has thereby been moved away from anvil 20 to the extent shown in FIG. 2b. The thread can now be placed into hook 60 of anvil 20. Gently tapping actuation pins 40, 41 in the circumferential direction displaces them into the central region of T-slot opening 26, and the relatively strong force of the cocked spring 54 ensures that actuation mechanism 30 is moved abruptly, i.e. in the manner of a guillotine, in the distal direction. As is evident from the reverse sequence of FIGS. 2b, 2a, and 2, blade 18 and its tip 64 thereby move very quickly toward the thread (not shown here) caught in hook 60 of anvil 20, immediately cutting through it. The impact of actuation mechanism 30 on the interior of wall 47 is damped by the compression of damping member 45.

Thread cutter 10 described here is designed as an individual instrument. It can also be configured as part of a multifunctional instrument which not only contains the thread cutter but also has a suturing apparatus.

What is claimed is:

1. A surgical thread cutter, having a blade movable via an actuation mechanism relative to an anvil toward and away from the latter, and having a spring by way of which spring said blade can be acted upon by a compressive spring force in one movement direction of said blade, wherein said spring acts upon said blade in a cutting direction, and wherein a retention system is provided by means of which said blade can be locked in a position remote from said anvil, and said force of said spring is set in such a way that after said retention system is released, said blade can be moved onto the anvil in the manner of a guillotine, said anvil being in the shape of a hook.

2. The surgical thread cutter of claim 1, wherein said actuation mechanism is movable along the movement direction of said blade, and said actuation mechanism is rotatable relative to said movement direction and can be retained by said retention system in a rotated position.

3. The surgical thread cutter of claim 1, wherein said actuation mechanism is received in a handle-like housing disposed at a proximal end of said cutter.

4. The surgical thread cutter of claim 1, wherein said retention mechanism has at least one actuation element projecting radially from said actuation mechanism, which at least one actuation element extends through a bayonet guide on a housing receiving said actuation element.

5. The surgical thread cutter of claim 4, wherein two diametrically opposite radially projecting actuation pins are provided.

6. The surgical thread cutter of claim 5, wherein said bayonet guide is configured as a T-shaped slot opening in said housing.

7. The surgical thread cutter of claim 6, wherein transverse regions of said T-shaped slot opening, which regions extend in a circumferential direction of said housing, are inclined somewhat in the direction of said anvil.

8. The surgical thread cutter of claim 1, wherein said spring is arranged in a handle-like housing receiving said actuation mechanism.

9. The surgical thread cutter of claim 1, wherein a damping member is provided which damps the movement of said blade at the end of a cutting movement.

10. The surgical thread cutter of claim 9, wherein said actuation mechanism has said damping member, which damps an impact of said actuation mechanism against a stop at the end of said cutting movement.

11. The surgical thread cutter of claim 1, wherein a damping member is provided in a housing receiving said actuation mechanism, said damping member is a elastic damping member which strikes against a wall of said housing and in that context is deformable.

12. The surgical thread cutter of claim 1, wherein said blade is received within a shaft, and said shaft and said blade are detachable from one another.

13. The surgical thread cutter of claim 10, wherein said anvil is part of said shaft, and said shaft can be detachably joined to a handle-like housing.

14. The surgical thread cutter of claim 1, wherein a tip of said hook faces toward a tip of said blade.

15. The surgical thread cutter of claim 1, wherein said anvil has a longitudinal slot into which said blade can be extended.

16. The surgical thread cutter of claim 1, wherein said blade runs along a surface of said anvil.

17. The surgical thread cutter of claim 1, wherein said blade has a cutting edge which coacts with an edge of said anvil.

18. The surgical thread cutter of claim 1, wherein a length of a moving path of said blade is adjustable.

19. The surgical thread cutter of claim 1, wherein said spring is configured as a helical spring.

20. The surgical thread cutter of claim 1, wherein said spring is configured as a compressed-air spring.

21. The surgical thread cutter of claim 1, wherein said spring is configured as a cocked spring.

22. The surgical thread cutter of claim 1, wherein it is part of a multifunctional instrument.

23. A surgical thread cutter comprising:

an elongated shaft having proximal and distal ends;

an anvil provided on the distal end of the elongated shaft;

a blade displaceable between a first position, wherein said blade is spaced from the anvil between the proximal and distal ends of the elongated shaft, and a second position, wherein the blade is displaced toward the distal end in a cutting direction onto the anvil;

a retention system connected to the blade for arresting the displacement of the blade in the cutting direction in said first position; and a compression spring compressed when said blade is in said first position biasing said blade toward said distal end when said blade is in the first position so as to enable said blade to move in the cutting direction onto the anvil in the manner of guillotine after the retention system has been released.

* * * * *